US011065027B2

(12) United States Patent
Franco et al.

(10) Patent No.: US 11,065,027 B2
(45) Date of Patent: Jul. 20, 2021

(54) METHOD AND APPARATUS FOR TISSUE COPYING AND GRAFTING

(71) Applicant: The General Hospital Corporation, Boston, MA (US)

(72) Inventors: Walfre Franco, Westborough, MA (US); Joel N. Jimenez-Lozano, Cambridge, MA (US); Martin Purschke, Boston, MA (US); Richard R. Anderson, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/800,081

(22) Filed: Jul. 15, 2015

(65) Prior Publication Data

US 2016/0015416 A1 Jan. 21, 2016

Related U.S. Application Data (60) Provisional application No. 62/024,524, filed on Jul. 15, 2014.

(51) Int. Cl.
*A61B 17/322* (2006.01)
*A61B 17/3205* (2006.01)
(Continued)

(52) U.S. Cl.
CPC ...... *A61B 17/32053* (2013.01); *A61B 17/322* (2013.01); *A61B 2017/00004* (2013.01);
(Continued)

(58) Field of Classification Search
CPC ............ A61B 17/322; A61B 17/32053; A61B 2017/00004; A61B 2017/00752;
(Continued)

(56) References Cited

U.S. PATENT DOCUMENTS

| 3,613,242 | A | * | 10/1971 | Hill | ...................... A61B 17/322 |
|---|---|---|---|---|---|
| | | | | | 30/295 |
| 5,647,857 | A | | 7/1997 | Anderson et al. | |

(Continued)

FOREIGN PATENT DOCUMENTS

| WO | WO-2007042818 A1 | 4/2007 | |
|---|---|---|---|
| WO | WO 2012103492 A1 * | 8/2012 | ........... A61B 17/205 |

(Continued)

OTHER PUBLICATIONS

International Search Report and Written Opinion issued by the U.S. Patent and Trademark Office as International Searching Authority for International Application No. PCT/US15/40536 dated Oct. 16, 2015 (9 pages).

(Continued)

*Primary Examiner* — Kathleen S Holwerda
(74) *Attorney, Agent, or Firm* — Quarles & Brady LLP (57) ABSTRACT

The present disclosure relates to exemplary embodiments of method and apparatus for harvesting, handling and implanting small tissue grafts obtained from a donor site. In some embodiments the apparatus includes hollow needles and base that can be formed of one or more biocompatible materials that are biodegradable and/or dissolvable.

20 Claims, 6 Drawing Sheets

(51) Int. Cl.
*A61B 17/32* (2006.01)
*A61B 17/00* (2006.01)
*A61B 90/00* (2016.01)
*A61F 2/10* (2006.01)
*A61B 17/30* (2006.01)

(52) U.S. Cl.
CPC ............... *A61B 2017/00752* (2013.01); *A61B 2017/00969* (2013.01); *A61B 2017/306* (2013.01); *A61B 2017/320064* (2013.01); *A61B 2090/033* (2016.02); *A61F 2/105* (2013.01)

(58) Field of Classification Search
CPC ......... A61B 2017/00969; A61B 2017/320064; A61B 5/150977; A61B 5/150984; A61B 2/104
USPC .................. 606/131–133, 186; 600/562–572
See application file for complete search history.

(56) References Cited

U.S. PATENT DOCUMENTS

| | | | |
|---|---|---|---|
| 5,919,196 A | 7/1999 | Bobic et al. | |
| 6,077,217 A | 6/2000 | Love et al. | |
| 6,440,086 B1 | 8/2002 | Hohenberg | |
| 6,997,923 B2 | 2/2006 | Anderson et al. | |
| 7,651,507 B2 | 1/2010 | Mishra et al. | |
| 7,926,401 B2 | 4/2011 | Mishra et al. | |
| 8,226,664 B2 | 7/2012 | Drews et al. | |
| 8,696,686 B2 | 4/2014 | Drews et al. | |
| 9,017,343 B2 | 4/2015 | Westerling, Jr. et al. | |
| 9,060,803 B2 | 6/2015 | Anderson et al. | |
| 9,084,465 B2 | 7/2015 | Oostman, Jr. et al. | |
| 9,119,945 B2 | 9/2015 | Simons et al. | |
| 2004/0116942 A1* | 6/2004 | Feller ............... | A61B 17/32053 606/133 |
| 2005/0143713 A1 | 6/2005 | Delmore et al. | |
| 2006/0155266 A1 | 7/2006 | Manstein et al. | |
| 2007/0043376 A1 | 2/2007 | Leatherbury et al. | |
| 2008/0200883 A1* | 8/2008 | Tomono ............ | A61M 37/0015 604/272 |
| 2008/0208146 A1 | 8/2008 | Brandwein et al. | |
| 2008/0234697 A1* | 9/2008 | DuBois ................. | A45D 26/00 606/133 |
| 2011/0313429 A1 | 12/2011 | Anderson et al. | |
| 2012/0029434 A1* | 2/2012 | Kobayashi ........ | A61M 37/0015 604/173 |
| 2012/0041430 A1 | 2/2012 | Anderson et al. | |
| 2012/0245612 A1 | 9/2012 | Keren et al. | |
| 2012/0271320 A1 | 10/2012 | Hall et al. | |
| 2013/0096678 A1 | 4/2013 | Denham | |
| 2014/0039523 A1* | 2/2014 | Austen ................. | A61B 17/205 606/131 |
| 2014/0200484 A1 | 7/2014 | Austen et al. | |
| 2014/0277055 A1* | 9/2014 | Austen, Jr. ............ | A61M 1/008 606/186 |
| 2015/0238214 A1 | 8/2015 | Anderson et al. | |
| 2015/0258319 A1 | 9/2015 | Simmers | |
| 2015/0320990 A1 | 11/2015 | Burton et al. | |
| 2016/0082241 A1 | 3/2016 | Burton et al. | |
| 2016/0121091 A1 | 5/2016 | Burton et al. | |
| 2016/0136406 A1 | 5/2016 | Berry et al. | |

FOREIGN PATENT DOCUMENTS

| | | | |
|---|---|---|---|
| WO | WO-2013013196 A1 * | 1/2013 | ............ A61M 1/008 |
| WO | WO-2013/151463 A2 | 10/2013 | |
| WO | WO-2014/028626 A1 | 2/2014 | |

OTHER PUBLICATIONS

Extended European Search Report issued in EP15822540.9; dated Feb. 22, 2018 (10 pages).

* cited by examiner

METHOD AND APPARATUS FOR TISSUE COPYING AND GRAFTING

REFERENCE TO RELATED APPLICATIONS

This application claims the benefit of U.S. Patent Application Ser. No. 62/024,524, filed on Jul. 15, 2014, and entitled Method and Apparatus for Tissue Copying and Grafting. The specification of the foregoing is incorporated by reference herein in its entirety.

GOVERNMENT SUPPORT

This invention was made with the Government support under Grant Number W911NF-11-1-0122 awarded by the U.S. Army Medical Research and Material Command. The Government has certain rights in this invention.

FIELD OF THE INVENTION

The present disclosure relates to exemplary embodiments of method and apparatus for harvesting, handling and implanting small tissue grafts obtained from a donor site.

BACKGROUND INFORMATION

An autograft can refer to tissue transplanted from one part of an individual's body (e.g., a "donor site") to another part (e.g., a "recipient site"). Autografts can be used, for example, to replace missing skin and other tissue and/or to accelerate healing resulting from trauma, wounds, burns, surgery and birth defects. Availability of tissue for autografting can be limited by characteristics of candidate donor sites, including a number and/or total area of tissue grafts, healing behavior of the donor site, similarity of the donor and recipient sites, aesthetic considerations, etc.

Skin grafting can be performed surgically. For example, a conventional autograft procedure may include excision or surgical removal of burn injured tissue, choosing a donor site, which may be an area from which healthy skin is removed to be used as cover for the cleaned burned area, and harvesting, where the graft may be removed from the donor site, e.g., using an instrument similar to an electric shaver. Such instrument (e.g., a dermatome) can be structured to gently shave a piece of tissue, which may be, e.g., about $10/1000$ of an inch thick for a split-thickness graft, from the skin at the unburned donor site to use as a skin graft. The skin graft can then be placed over the cleaned wound so that it can heal. Donor skin tissue can be removed to such a depth that the donor site can heal on its own, in a process similar to that of healing of a second degree burn.

Two conventional types of autografts which may be used for a permanent wound coverage include sheet grafts and meshed grafts. A sheet graft can refer to a piece of skin tissue removed from an undamaged donor site of the body, in a process that may be referred to as harvesting. The size of the donor skin piece that is used may be about the same size as the damaged area. The sheet graft can be laid over the excised wound, and stapled or otherwise fastened in place. The donor skin tissue used in sheet grafts may not stretch significantly, and a sheet graft can be obtained that is slightly larger than the damaged area to be covered because there may often be a slight shrinkage of the graft tissue after harvesting.

Sheet grafts can provide an improved appearance of the repaired tissue site. For example, sheet grafts may be preferred for use on large areas of the face, neck and hands if they are damaged, so that these more visible parts of the body can appear less scarred after healing. A sheet graft may be used to cover an entire burned or damaged region of skin, e.g., if the damaged site is small. Small areas of a sheet graft can be lost after placement because of a buildup of fluid (e.g., a hematoma) can occur under the sheet graft following placement the sheet graft.

Sheet grafts may be full-thickness or split-thickness. For example, split-thickness skin grafts can be used to cover wounds in burn and skin ulcer patients. A conventional split-thickness graft can be formed, e.g., by harvesting a sheet of epidermis and upper dermal tissue from a donor site, in a procedure similar to that of peeling an apple. The split-thickness graft can then be placed on the location of the burn or ulcer. The skin tissue may then grow back at the donor site following a generally extended healing time. Split-thickness grafts may be preferable to full-thickness grafts because removing large amounts of full-thickness skin tissue from the donor site can lead to scarring and extensive healing times at the donor site, as well as an increased risk of infection. However, skin tissue removed from the donor site for a split-thickness skin autograft can include only a thin epithelial layer, which can lack certain elements of the dermis that improve structural stability and normal appearance in the recipient site.

Full-thickness skin grafts can be formed using sheets of tissue that include the entire epidermis layer and a dermal component of variable thickness. Because the dermal component can be preserved in full-thickness grafts, more of the characteristics of normal skin can be maintained following the grafting procedure. Full-thickness grafts can contain a greater collagen content, dermal vascular plexus, and epithelial appendages as compared to split-thickness grafts. However, full-thickness grafts can require more precise conditions for survival because of the greater amount of tissue requiring revascularization.

Full-thickness skin grafts can be preferable for repairing, e.g., visible areas of the face that may be inaccessible by local flaps, or for graft procedures where local flaps are contraindicated. Such full-thickness skin grafts can retain more of the characteristics of normal skin including, e.g., color, texture, and thickness, as compared to split-thickness grafts. Full-thickness grafts may also undergo less contraction while healing. These properties can be important on more visible areas such as the face and hands. Additionally, full-thickness grafts in children can be more likely to grow with the individual. However, application of conventional full-thickness skin grafts can be limited to relatively small, uncontaminated, well-vascularized wounds, and thus may not be appropriate for as many types of graft procedures as split-thickness grafts. Additionally, donor sites for full-thickness grafts can require surgical closure or resurfacing with a split-thickness graft.

A meshed skin graft can be used to cover larger areas of open wounds that may be difficult to cover using sheet grafts because of, e.g., a lack of a sufficient area of healthy donor sites. Meshing of a skin graft can facilitate skin tissue from a donor site to be expanded to cover a larger area. It also can facilitate draining of blood and body fluids from under the skin grafts when they are placed on a wound, which may help prevent graft loss. The expansion ratio (e.g., a ratio of the unstretched graft area to the stretched graft area) of a meshed graft may typically be between about 1:1 to 1:4. For example, donor skin can be meshed at a ratio of about 1:1 or 1:2 ratio, whereas larger expansion ratios may lead to a more fragile graft, scarring of the meshed graft as it heals, and/or extended healing times.

A conventional graft meshing procedure can include running the donor skin tissue through a machine that cuts slits through the tissue, which can facilitate the expansion in a pattern similar to that of fish netting or a chain-link fence. Healing can occur as the spaces between the mesh of the stretched graft, which may be referred to as gaps or interstices, fill in with new epithelial skin growth. However, meshed grafts may be less durable graft than sheet grafts, and a large mesh can lead to permanent scarring after the graft heals.

To help the graft heal and become secure, the area of the graft can preferably not be moved for at least about five days following each surgery. During this immobilization period, blood vessels can grow from underlying tissue into the skin graft, and can help to bond the two tissue layers together. About five days after the graft is placed, exercise therapy programs, tub baths, and other normal daily activities can often be resumed. Deep second-degree and full-thickness burns may require skin graft surgery for quick healing and minimal scarring. Large burn sizes can lead to more than one grafting procedure during a hospital stay, and may require long periods of immobilization for healing.

As an alternative to autografting, skin tissue obtained from recently-deceased people (which may be referred to, e.g. as a homograft, an allograft, or cadaver skin) can be used as a temporary cover for a wound area that has been cleaned. Unmeshed cadaver skin can be put over the excised wound and stapled in place. Post-operatively, the cadaver skin may be covered with a dressing. Wound coverage using cadaveric allograft can then be removed prior to permanent autografting.

A xenograft or heterograft can refer to skin taken from one of a variety of animals, for example, a pig. Heterograft skin tissue can also be used for temporary coverage of an excised wound prior to placement of a more permanent autograft, and may be used because of a limited availability and/or high expense of human skin tissue. In some cases religious, financial, or cultural objections to the use of human cadaver skin may also be factors leading to use of a heterograft. Wound coverage using a xenograft or an allograft is generally a temporary procedure which may be used until harvesting and placement of an autograft is feasible.

Epithelial appendages can preferably be regenerated following a grafting procedure. For example, hair can be more likely to grow from full-thickness grafts than from split-thickness grafts, but such hair growth may be undesirable based on the location of the wound. Accordingly, donor sites for full-thickness grafts can be carefully selected based in part, e.g., on patterns of hair growth at the time of surgery. Further, certain hair follicles may not be oriented perpendicular to the skin surface, and they can be transected if an incision provided to remove graft tissue is not oriented properly.

Sweat glands and sebaceous glands located in graft tissue may initially degenerate following grafting. These structures can be more likely to regenerate in full-thickness grafts than in split-thickness grafts because full-thickness grafts can be transferred as entire functional units. For example, sweat gland regeneration can depend in part on reinnervation of the skin graft with recipient bed sympathetic nerve fibers. Once such ingrowth has occurred, the skin graft can assume the sweating characteristics of the recipient site, rather than retaining the characteristics of the donor site. In contrast, sebaceous gland regeneration may be independent of graft reinnervation and can retain the characteristics of the donor site. Prior to the regeneration, the skin graft tissue may lack normal lubrication of sebum produced by these glands, which can make such grafts more susceptible to injury.

In general, grafting procedures may be limited by the amount of tissue which can be removed from the donor site without causing excessive adverse effects. Full-thickness grafts can provide improved tissue quality at the wound site, but the donor site may be more severely disfigured as described above. Split-thickness grafts can be a compromise between healing times and aesthetic and functional properties of the donor and recipient sites, whereas meshing can provide more extensive graft coverage at the expense of visible scarring.

Harvesting of graft tissue from the donor site generally can generate undesirable large-scale tissue damage to the donor site. On the other hand, small areas of skin wounding adjacent to healthy tissue can be well-tolerated and may heal quickly. Such healing of small wounds can occur in techniques such as "fractional photothermolysis" or "fractional resurfacing," in which patterns of damage having a small dimension can be created in skin tissue. These exemplary techniques are described, e.g., in U.S. Pat. No. 6,997,923 and U.S. Patent Publication No. 2006/0155266. Small-scale damage patterns can heal quickly by regrowth of healthy tissue, and can further provide desirable effects such as skin tightening without visible scarring. Accordingly, removal of small tissue samples, e.g., having a width or diameter of less than about 2 mm, or preferably less than about 1 mm, can provide healthy tissue that can be used for grafting purposes while facilitating rapid, scar-free healing of a donor site. Such small tissue samples, referred to as microscopic tissue columns or MTCs, can be obtained from skin, various organs, muscle tissue, or any other body tissue to be grafted.

Tissue copying is another area of increasing interest, in which samples of different types of tissue can be "grown" ex vivo, e.g., on supporting scaffolds or in matrices. A suitable growth environment is typically provided to promote cell growth and replication; such environment can provide a particular temperature and pH, moisture, salinity level, oxygen, nutrients, etc. However, 'seeding' of such scaffolds or matrices with tissue samples can be challenging, as it may be desirable to harvest many cells and disperse them uniformly in or on the supporting structures to promote viability and rapid growth.

Harvesting or removal of such small tissue samples, e.g., MTCs, can be performed using coring needles, biopsy needles, or the like. However, handling of the MTCs can present many challenges, including preventing mechanical damage and/or contamination of the tissue, storing of the small tissue portions after removal from the donor site, and insertion of the MTCs into a recipient site.

In view of the shortcomings of the above described procedures for tissue grafting and copying, it may be desirable to provide exemplary embodiments of method and apparatus that can provide improved handling and implantation of microscopic tissue columns suitable for grafting and tissue copying procedures.

SUMMARY OF EXEMPLARY EMBODIMENTS

Exemplary embodiments of the present disclosure provide method and apparatus for obtaining small portions of graft tissue (e.g., micrografts) that can be accompanied by rapid healing of the donor site, handling of such micrografts, and implantation of the micrografts into a recipient site or an ex vivo matrix for tissue copying. Such micrografts can comprise skin tissue that can include, e.g., epidermal and dermal tissue, and/or tissue obtained from other body organs and structures.

The micrografts can have at least one dimension that is relatively small, e.g., less than about 1 mm, or less than about 0.5 mm, or optionally about 0.3 mm or less, or about 0.2 mm. Such exemplary small dimensions of the micrografts can facilitate both healing of the donor site following harvesting and viability of the micrografts by allowing greater diffusional nourishment of the micrograft tissue. The small regions of damage in the donor site caused by a removal of the tissue portions can heal rapidly with little or no formation of visible scars. The micrografts obtained from skin tissue can include, e.g., epidermal and dermal tissue, and can also include stem cells that can be located proximal to the dermal/fatty layer boundary. The micrografts can also be obtained from other types of tissue, e.g., various internal organs or the like. A fraction of dermal tissue that is removed from a donor site can be, e.g., less than about 50%, although other fractions may be used.

An exemplary embodiment of the apparatus can be provided for harvesting micrografts that can include at least one hollow needle or tube. An inner diameter of the hollow needle can be approximately the same size as a diameter or width of the micrograft to be harvested. A distal end of the hollow needle can have two or more points to facilitate separation of the micrografts from the surrounding tissue. A collar can be provided on the exterior of the needle to control or limit the penetration depth of the needles into the tissue of a donor site. A plate can be provided in the needle, e.g., that can partially or completely obstruct the lumen at a particular location. The plate can be used to retain a micrograft in the distal portion of the needle when the needle is e-inserted into a recipient site or matrix.

A further exemplary embodiment of the apparatus can be provided that includes a plurality of such hollow needles or tubes for simultaneous harvesting of a plurality of micrografts. The hollow needles can be affixed to a base, and an optional housing can be coupled or removably affixed to the base to facilitate manipulation of the base and needles. In certain embodiments, the base can also be made of a biodegradable or dissolvable material.

The hollow needles and base, if present, can be formed of one or more biocompatible materials that are biodegradable and/or dissolvable. The degradation or dissolution of such materials can be activated by exposure to biological tissue, moisture, light, heat, and/or certain chemical compositions or environments. The materials can be selected to have sufficient mechanical strength to withstand insertion into biological tissue without breaking or deforming significantly. In certain embodiments, the material used to form the needles can be porous to facilitate dissolution of the needles and/or transport of nutrients and the like to the micrografts within the needles.

The micrografts can be harvested from the donor site by inserting the exemplary apparatus into tissue at the donor site to a particular depth thereof, and then removing the apparatus, such that a micrograft is separated from the surrounding tissue and retained in the distal portion of the needles. The apparatus can then be inserted in a recipient site. In certain embodiments, the entire apparatus can remain on the recipient site. In further embodiments, the base and/or upper portion of the needles can be broken off such that only the distal portion of the needle(s) containing a micrograft remain embedded in the tissue at the recipient site. Over a period of time, which can range from minutes to many hours or more, the needle material can dissolve, thereby safely implanting the micrograft(s) into the recipient site.

In further embodiments, the exemplary micrografts can be implanted in a biocompatible matrix that can be maintained under favorable cell growth conditions, e.g., to promote growth and division of the cells in the micrografts and generate a "copy" of the harvested tissue. The biocompatible matrix can be formed using collagen, polylactic acid, hyaluronic acid, and/or other substances which can support the harvested micrograft tissue portions and promote their growth. The matrix can optionally include, e.g., nutrients and/or other substances to promote tissue growth.

These and other objects, features and advantages of the present disclosure will become apparent upon reading the following detailed description of exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF EXEMPLARY EMBODIMENTS

Figure 1A:
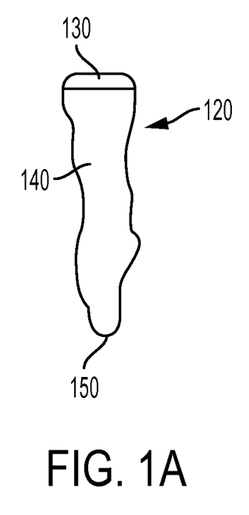
FIG. 1A is a schematic illustration of an exemplary micrograft that may be removed from the exemplary donor site shown in FIG. 1A.

Exemplary embodiments of the present disclosure can provide a method and apparatus for harvesting, handling and/or implanting tissue portions having at least one small dimension (e.g., micrografts, microscopic tissue columns, or MTCs). An exemplary MTC 120 obtained from skin tissue is shown in FIG. 1A. The exemplary MTC 120 can have an elongated shape that may be approximately cylindrical. The MTC 120 can include both epidermal tissue 130 and dermal tissue 140 from the exemplary donor site 100. For example, the exemplary micrograft 120 can be about 3 mm in length, which can correspond to a typical total depth of the skin layer (e.g., epidermal and dermal layers). A lower portion 150 of the exemplary MTC 120 obtained from skin tissue may also include stem cells that can be present in a lower portion of the dermal layer of the skin (e.g., near a dermal/fatty layer boundary).

A width or diameter of the exemplary MTCs obtained during a harvesting procedure can be less than about 1 mm, or less than about 0.5 mm. In certain exemplary embodiments, the diameter or width can be less than about 0.3 mm, or about 0.2 mm. The particular width or diameter of an MTC 120 can be selected, e.g., based on the effects of creating small holes in a donor site that can heal rapidly and/or without scarring, and on creating portions of tissue that may be large enough to retain a sufficient amount of tissue and/or local tissue structures to provide suitable grafting results.

For example, living tissue can be provided with nutrients via a diffusional transport over distances of about 0.1 mm. Accordingly, the exemplary micrografts 120 having at least one dimension that is less than about 0.3 mm or, e.g., about 0.2 mm, can exhibit improved viability and likelihood to survive, and grow when used in a graft. Such exemplary micrografts 120 can be better able to receive nutrients (including, e.g., oxygen) when placed in a recipient site, prior to revascularization of the tissue. Somewhat larger micrografts 120, e.g., having a width or diameter up to about 1-2 mm, can also benefit from such diffusional transport of nutrients, and can also be more likely to survive than conventional macroscopic pieces of graft tissue (e.g., conventional full-thickness, split-thickness, or meshed grafts).

Figure 1B:
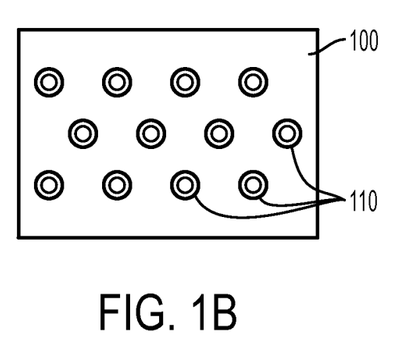
FIG. 1B is a schematic illustration of an exemplary donor site after cylindrical portions of micrograft tissue have been harvested therefrom.

A top view of an exemplary donor site 100, from which several MTCs have been harvested or removed, is shown in FIG. 1B. The holes 110 shown in FIG. 1B represent regions of the exemplary donor site 100 from which the small tissue portions or columns 120 (e.g., micrografts) have been removed. These exemplary holes 110 may have an approximately round cross-sectional shape, although other shapes may be used in further embodiments of the disclosure.

Removal of one or more MTCs 120 from the donor site 100 can facilitate rapid healing of the donor site 100 while providing improved or desirable tissue characteristics or changes at a recipient site. For example, the small holes or regions of damage 110 created at the donor site 100 by the removed tissue can heal rapidly and/or without visible scarring.

A fraction of surface tissue removed from the donor site 100 by harvesting (which can correspond to a fractional surface area of the exemplary donor site 100 occupied by the holes 110) may be generally less than about 50%. The fraction of tissue removed can be sufficiently large to provide enough harvested micrografts 120 to form a graft therefrom of appropriate size, but small enough to facilitate rapid healing at the donor site 100 based on growth from the remaining undamaged tissue. Other fractions of tissue can be removed from a donor site 100 depending on factors such as, e.g., the particular characteristics of the donor site 100, the size of the graft needed, and the overall amount of donor site tissue available.

Figure 2A:
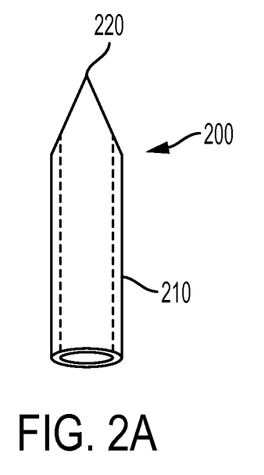
FIG. 2A is an exemplary illustration of a distal end of a harvesting needle that includes two points.
Figure 2B:
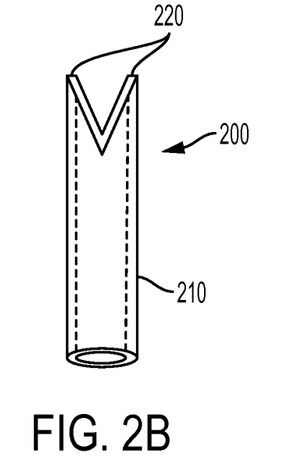
FIG. 2B is another side view of the distal end of the harvesting needle shown in FIG. 2A.
Figure 2C:
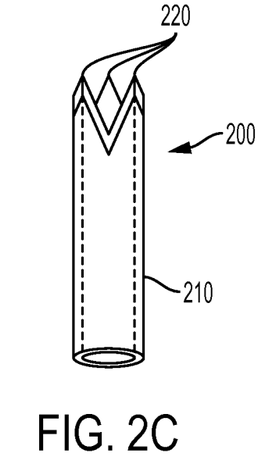
FIG. 2C is an exemplary illustration of a distal end of a further harvesting needle that includes three points.

In exemplary embodiments of the present disclosure, a harvesting needle apparatus 200 can be provided, such as that shown in FIGS. 2A and 2B, which can facilitate harvesting of the exemplary micrografts 120 from the donor site 100 as described herein. The exemplary apparatus 200 can include a hollow needle or tube 210. A distal end of the tube 210 can be shaped to form a plurality of points 220. For example, the two exemplary points or extensions 220 can be formed by grinding or cutting opposite sides of the tube 210 at an angle relative to the long axis of the tube 210, as shown in FIG. 2A. The side view of the needle 210 shown in FIG. 2B illustrates the two points 220 formed by the beveled cuts. The beveled shape of these points 220 can facilitate insertion of the needle 210 into a biological tissue and separation of the tissue portion in the central lumen of the needle 210 from the surrounding tissue to form a MTC or micrograft. In a further exemplary embodiment, shown in FIG. 2C, the apparatus 200 can be provided with three points 220 at a distal end thereof, e.g., by grinding or cutting the end of the tube 210 at three orientations spaced apart by about 120 degrees around the axis of the tube 210. In still further exemplary embodiments, the apparatus 200 can be provided with more than three points 220 provided at a distal end thereof, e.g., with four, five, or more points 220.

The inner diameter of the tube 210 can be selected to approximately correspond to a particular diameter of a micrograft 120 to be removed from the donor site 100 as described herein. For example, a tube 210 having a size of 18 or 20 gauge (e.g., having an inner diameter of 0.838 mm and 0.564 mm, respectively) or the like can be used to form the tube. A tube 210 having a larger gauge (e.g., having a smaller inner diameter) can also be used in certain embodiments. A width or diameter of the harvested micrograft 120 can be about the same width or slightly smaller than the inside diameter of the needle 210 used to harvest it.

For example, a hollow needle 210 that can be used to obtain or harvest MTCs 120 from skin tissue and protect them after harvesting, e.g., while manipulating them and/or implanting them in a recipient site, can have a penetration length of about 2-3 mm, an outer diameter of about 1 mm or less, and an inner lumen diameter of less that about 0.8 mm, e.g., between about 0.1 mm and 0.5 mm.

In exemplary embodiments of the present disclosure, at least a distal portion of the hollow needle 210 (e.g., a portion of the hollow needle 210 at the end that includes points 220) can be formed of a material that is biocompatible and biodegradable or dissolvable. In certain embodiments, the entire hollow needle 210 can be formed of a biodegradable or dissolvable material. Biocompatibility may refer to the property of a material to contact a biological tissue or material, and/or perform a function with respect to a medical therapy, without eliciting any undesirable local or systemic effect in the recipient or beneficiary of that contact or therapy. Biodegradability can refer to the ability of a material to break down and lose its initial structural and/or compositional integrity (e.g., dissolve) when placed in contact with a biological system or component thereof, e.g., water or a saline solution. Dissolvability can refer to the ability of a material to decompose and break down when exposed to water or an aqueous environment, e.g., including contact with biological tissue.

For example, materials used to form at least a portion of the needle 210 are preferably non-toxic, have mechanical properties (e.g., stiffness, toughness, etc.) sufficient to facilitate insertion of the needle 210 into a biological tissue without undesirable breakage or deformation of the needle 210. For example, excessive deformation of the needle 210 during insertion into tissue could distort or close off the needle lumen, thereby preventing or inhibiting the separation and removal of a micrograft 120 from surrounding tissue in the donor site 100. The needle material(s) can also be capable of degradation or dissolution when contacting tissue or wetted, optionally at a known rate. In further embodiments, these materials can be activated to dissolve or decompose by chemical, biological, and/or physical mechanisms. Activators for such dissolution mechanisms can include application of light energy, e.g., light having one or more particular wavelengths, application of heat, and exposure to excess water or some other biocompatible solvent.

The dissolution time of a needle 210 can be based on several factors including, but not limited to, the diameter of the needle 210 and wall thickness, the particular material or composition used, the use and timing of any activators applied to enhance dissolution or degradation, etc. For example, a dissolution time for a needle 210 after insertion into a recipient site 400 can be on the order of about a minute or more, up to several hours or even a day or two. The dissolution time is preferably long enough to avoid premature weakening or breakdown of the needles 210 during the harvesting and implantation processes, but not so long as to reduce the viability or limit growth of the micrografts 120 after the needles 210 are inserted into a recipient site 400. Exemplary materials and further characteristics thereof are described in more detail herein below.

Figure 3:
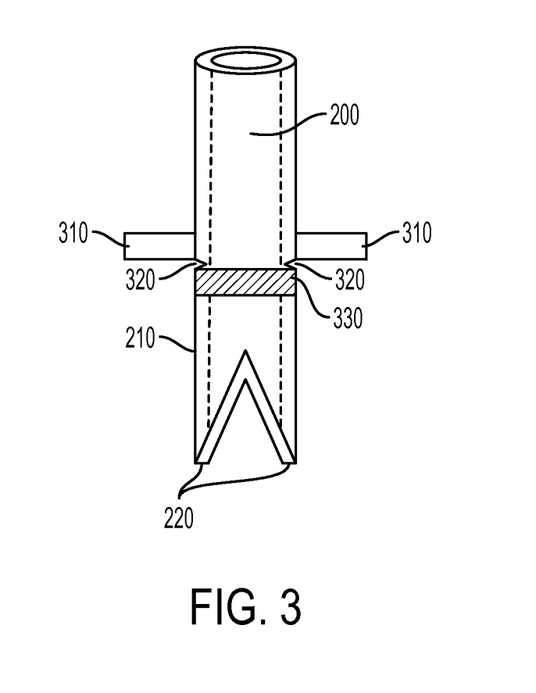
FIG. 3 is a schematic illustration of an exemplary apparatus that can be used to harvest and implant micrograft tissue in accordance with exemplary embodiments of the present disclosure.

The needle 210 can be provided with a collar arrangement 310 on an outer surface thereof, e.g., as shown in FIG. 3. The exemplary collar 310 can include one or more protrusions affixed to the needle 210 at a particular distance from the points 220, or alternatively it can be formed as a ring or bulge that surrounds the entire needle 210. The collar 310 can limit the penetration of the needle 210 to a particular depth. For example, such depth can approximately correspond to a desired length of the micrografts or MTCs 120 to be harvested by the needle 210. In further embodiments, this distance may be adjustable over a range of lengths, e.g., by moving the stop 310 along the axis of the needle 210, where the stop 310 can be frictionally or movably coupled to the needle 210.

In certain embodiments, the needle 210 can include one or more notches 320, e.g., as shown in FIG. 3. Such notches 320 can be provided below the stop 310, if present, above the stop 310, or at another location along the length of the needle 210. The notches 320 can be provided at one or more locations around the circumference of the needle 210, e.g. as a plurality of indentations or as a groove that extends partially or completely around the circumference of the needle 210. The notches 320 can facilitate breakage of the needle 210 at a particular location, e.g., to remove a proximal portion of the needle 210 while retaining a distal portion of the needle 210 within a biological tissue as described herein.

An optional plate 330 can be provided in the lumen of the needle 210 in certain exemplary embodiments, as shown in FIG. 3. The plate 330 can span the entire lumen, or alternatively it can obstruct a portion thereof. The plate 330 can facilitate retention of an MTC 120 within the lower portion of the lumen. For example, the plate 330 can prevent an MTC from being pushed upward within the lumen when the needle 210 containing the MTC 120 is inserted into a donor site as described herein.

Figure 4A:
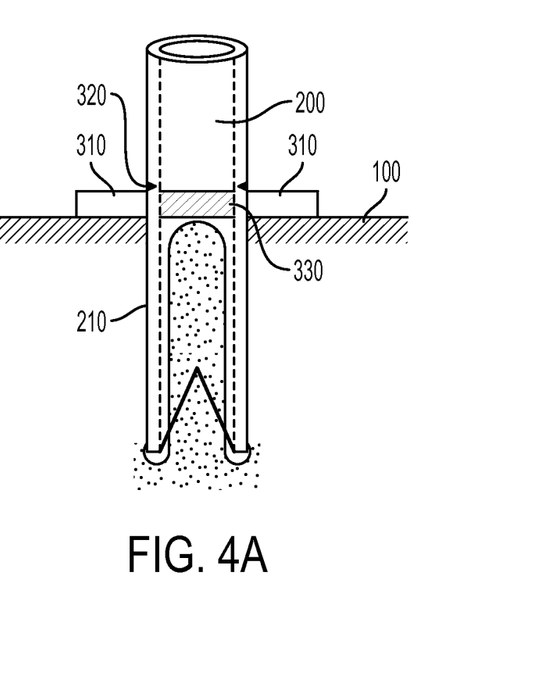
FIGS. 4A-4E show an exemplary procedural sequence for harvesting and implanting a micrograft in accordance with embodiments of the present disclosure.
Figure 4B:
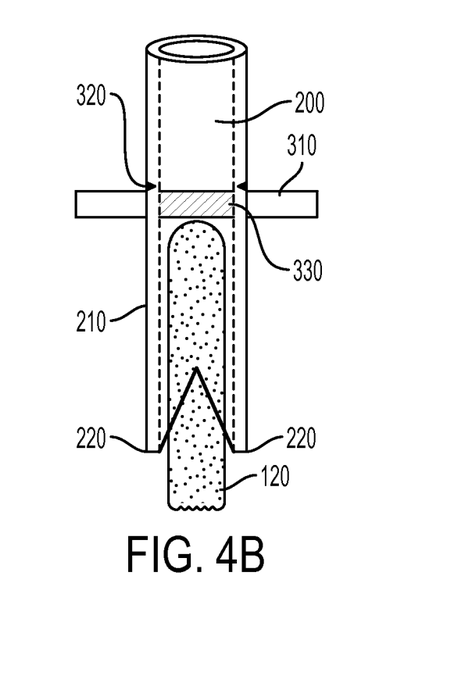

FIGS. 4A-4E illustrate an exemplary harvesting and implantation procedure in accordance with embodiments of the present disclosure. FIG. 4A shows an exemplary needle 210 after it has been inserted into the tissue at the donor site 100. The points 220 may facilitate such insertion and, together with the adjacent beveled edge, if present, can separate a portion of the donor site tissue within the central lumen from the surrounding tissue. Such tissue can be separated from the donor site 100 and remain within the needle 210 to form the micrograft 120, e.g., after the hollow needle 210 is removed from the donor site 100 as shown in FIG. 4B. If the donor site 120 is skin tissue, for example, the exemplary micrograft 120 thus formed can include both epidermal tissue 130 and dermal tissue 140. The micrograft 120 can be removed and retained within the lumen of the needle 210, e.g., based on friction between the MTC 120 and the inner walls of the needle 210.

Figure 4C:
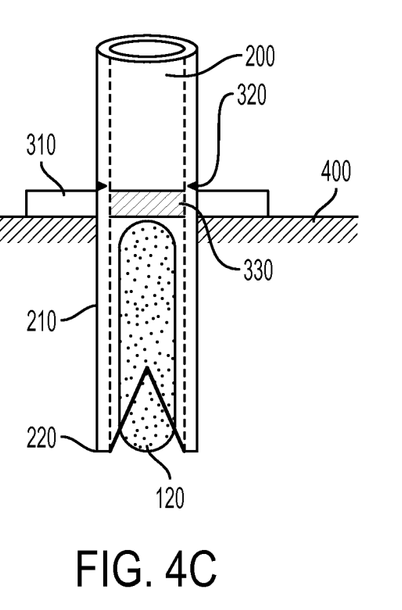
Figure 4D:
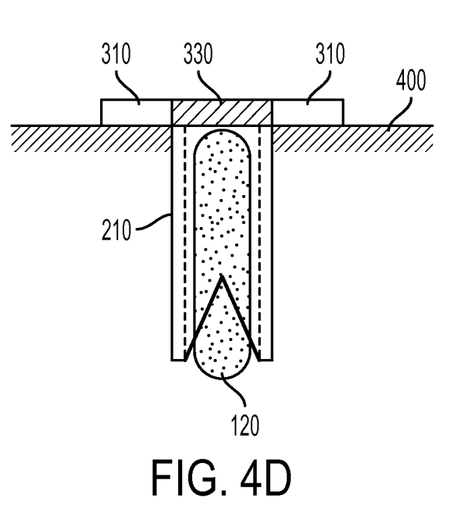

In FIG. 4C, the needle 210 containing the micrograft 120 has been inserted into tissue at a recipient site 400, optionally to the same or similar depth as the insertion depth shown in FIG. 4A. For example, a collar arrangement 310, if present, can facilitate a consistent insertion depth of the needle 210 into the biological tissue at the donor site 100 and recipient site 400. In FIG. 4D, the proximal portion of the needle 210 protruding above the recipient site 400 has been broken off, e.g., facilitated by the notches 320. The plate 330 and collar 310 remain with the needle 210 at the recipient site 400 in the exemplary procedure shown in FIG. 4D, and these components can protect the upper portion of the micrograft 120 within the recipient site 400. In further embodiments, the upper portion of the needle 210 can be broken off to remove the plate 330 and/or collar 310, e.g., such that only the distal portion of the needle 210 containing the micrograft 120 remains in the recipient site 400.

Figure 4E:
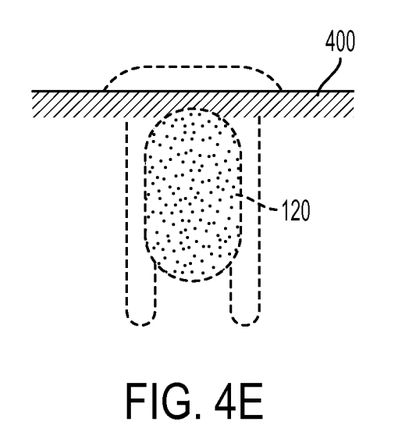

FIG. 4E shows the recipient site 400 some time after the needle 210 containing the micrograft 120 has been inserted therein. The needle 210 has substantially dissolved or degraded, as indicated by the dashed lines, and the micrograft 120 has become integrated with the surrounding tissue in the donor site 400. The plate 330, if present, can also be formed of a biodegradable material, such that it may also dissolve over time.

It can be readily appreciated when viewing the exemplary sequence in FIGS. 4A-4E that the micrograft or MTC 120 retains the same orientation in the recipient site 400 that it had in the donor site 100. Further, the micrograft 120 can be removed and implanted with minimal disruption, e.g., it remains within the lumen of the needle 210, thereby reducing any mechanical forces exerted on it and protecting it from the external environment during the harvesting, transportation, and implantation procedures. Such protection of the MTC 120 can increase its viability and likelihood of survival at the recipient site 400, and reduce the risk of contamination or infection during the procedure.

Exemplary procedures for harvesting and implanting the micrografts 120 described herein can be used to provide the micrografts 120 directly into, e.g., substantially whole tissue at the recipient site 400. For example, the micrografts 120 can be harvested from the donor site 100 that may contain melanocytes, and inserted directly into tissue at a recipient site that lacks sufficient melanocytes. Such exemplary procedure can be used to repigment skin tissue, e.g., to treat vitiligo or similar conditions. The exemplary micrografts 120 can also be harvested from a healthy donor site 100 and placed directly into scar tissue to facilitate growth of healthy tissue in the scar.

Figure 5A:
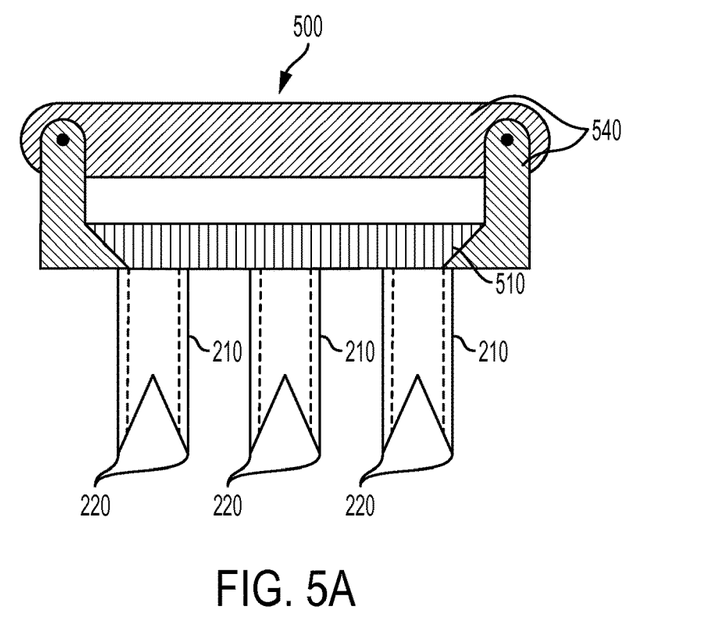
FIG. 5A is a schematic illustration of a further exemplary apparatus that can be used to harvest and implant micrograft tissue in accordance with further exemplary embodiments of the present disclosure.

In a further exemplary embodiment of the present disclosure, an exemplary apparatus 500 can be provided as shown in FIG. 5A. The apparatus 500 can include, e.g., a plurality of needles 210 affixed or mechanically coupled to a base 510. The number of needles 210 provided in the exemplary apparatus 500 can be, for example, greater than ten needles 210, or more than about 30 needles 210 in certain embodiments.

The exemplary apparatus 500 can be used to simultaneously obtain a plurality of the micrografts 120 in the plurality of the tubes 210. Exemplary procedures for harvesting/removal and/or implantation of such micrografts 120 using the exemplary apparatus 500 can be similar to the procedures described herein for obtaining single micrografts 120 using the exemplary single needle 210, e.g., as shown in FIGS. 4A-4E.

Figure 6A:
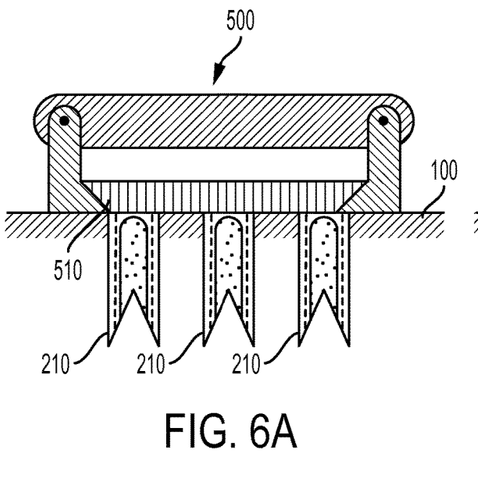
FIGS. 6A-6B show an exemplary procedural sequence for harvesting and implanting a micrograft in accordance with further embodiments of the present disclosure
Figure 6B:
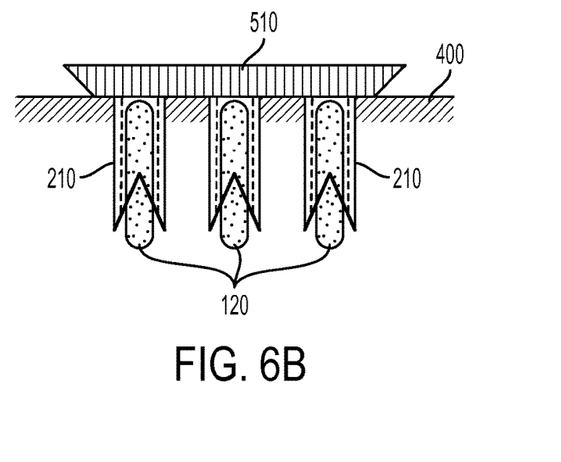

The base 510 can provide several functions. For example, in addition to providing a stable platform to anchor the plurality of needles 210 and maintain them in a particular location relative to one another, the base 510 can also control or limit the depth of penetration of the needles 210. The length of the needles 210 protruding from the base 510 can correspond to the depth of penetration when the apparatus 500 is pressed onto a donor site 100 as shown in FIG. 6A and/or into a recipient site 400 as shown in FIG. 6B. Further, the needles 210 can be formed as extensions of the base 510 or affixed thereto, such that the lumen of the needles 210 has a closed end at the base 510. In this manner, the base 510 can provide a similar function as the plate 330, e.g., retaining the MTCs 120 in the distal portion of the needles 210 after they are separated from the recipient site 100.

Figure 5B:
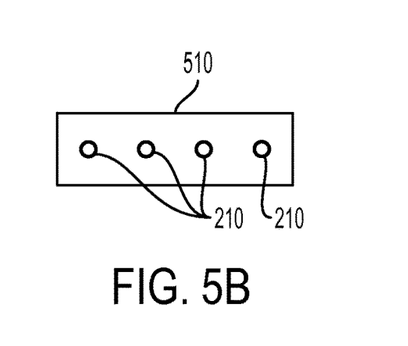
FIG. 5B is a schematic bottom view of a first exemplary arrangement of needles that can be used with the exemplary apparatus shown in FIG. 5A.
Figure 5C:
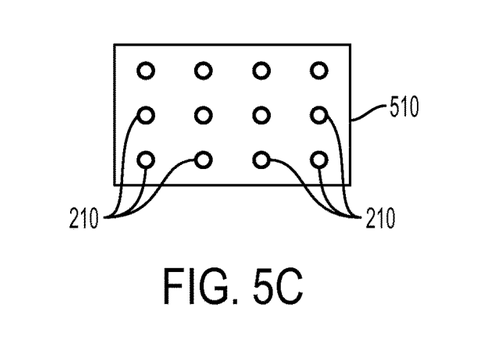
FIG. 5C is a schematic bottom view of a second exemplary arrangement of needles that can be used with the exemplary apparatus shown in FIG. 5A.
Figure 5D:
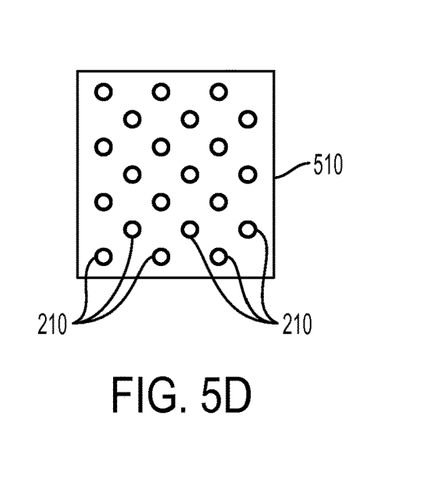
FIG. 5D is a schematic bottom view of a third exemplary arrangement of needles that can be used with the exemplary apparatus shown in FIG. 5A.
Figure 5E:
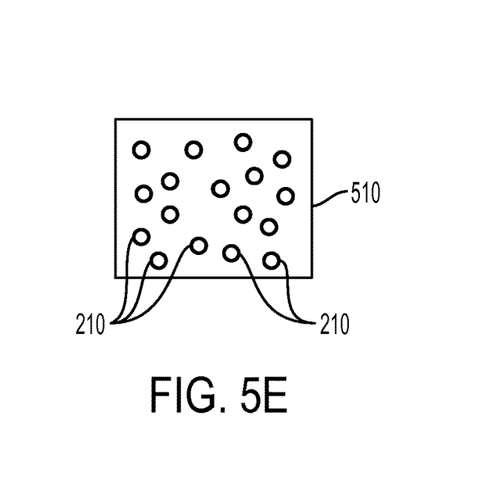
FIG. 5E is a schematic bottom view of a fourth exemplary arrangement of needles that can be used with the exemplary apparatus shown in FIG. 5A.

The needles 210 can be provided in various configurations, e.g., in a linear array, or in any one of various two-dimensional patterns along the base 510. Several exemplary configurations of the needles 210 on the base 510 are shown in FIGS. 5B-5E, including a linear array as shown in FIG. 5B, a square array as shown in FIG. 5C, a triangular or hexagonal array as shown in FIG. 5D, and an irregular pattern as shown in FIG. 5E. The base 510 can be provided in any of a variety of shapes. The particular shape can be, e.g., based on the size, shape, and location of the donor site 100 and/or recipient site 400. For example, the base 510 can be rectangular, square, round, oval, hexagonal, or another shape. As described herein, the apparatus 500 can include any number of needles 210, where such number may be selected based on factors such as the area of the donor site 100 and recipient site 400, the desired spacing or density of the needles 210 (and correspondingly, of the harvested and implanted MTCs 120), etc.

In further exemplary embodiments of the disclosure, a housing 540 can be provided with the apparatus 500. The housing 500 can be detachably coupled to the base 510, e.g., using a spring-loaded clamp, a frictional fit, an adhesive, or the like. The housing 540 can provide a variety of uses for the apparatus 500. For example, it can provide a gripping body or handle to facilitate manipulation of the base 510 and attached needles 210. The housing 540 can also provide mechanical support, e.g., for embodiments in which the base 510 may be thin, flexible, or relatively brittle. The housing 540 can optionally be reusable, wherein the needles 210 and/or the base 510 may generally be single-use or disposable.

FIGS. 6A and 6B illustrate an exemplary harvesting and implantation procedure in accordance with embodiments of the present disclosure. This procedure can be similar to that illustrated in FIGS. 4A-4E. For example, FIG. 6A shows an exemplary apparatus 500 comprising a plurality of needles 210 after it has been inserted into tissue at a donor site 100. A portion of the donor site tissue can be retained within the lumen of each needle 210, as described herein, to form the micrografts 120 after the apparatus 500 is withdrawn from the donor site 100.

In FIG. 6B, the apparatus 500 containing the micrograft 120 has been inserted into tissue at a recipient site 400, and the housing 540 has been removed from the apparatus 500 after insertion. The apparatus 500 can be pressed into the recipient site 400 (as well as into the donor site 100) until the base 510 contacts the tissue surface. Over time, the needles 210 can dissolve within the surrounding tissue, leaving the MTCs 120 in the recipient site 400.

Figure 7:
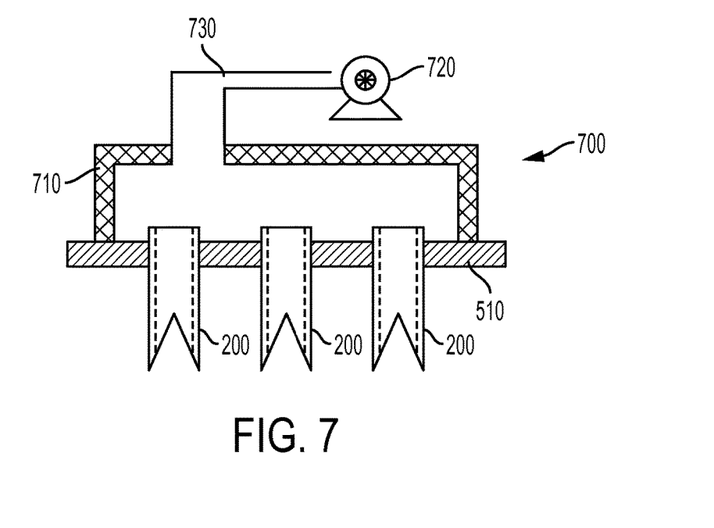
FIG. 7 is a schematic illustration of a still further exemplary apparatus that can be used to harvest and implant micrograft tissue in accordance with further exemplary embodiments of the present disclosure.

In a further exemplary embodiment of the present disclosure, an exemplary apparatus 700 can be provided as shown in FIG. 7. The apparatus 700 can include, e.g., a plurality of dissolvable tubes or hollow needles 210 that are affixed or mechanically coupled to a base 510. The tubes 210 can be provided in various configurations, e.g., in a linear array, or in any one of various two-dimensional patterns along the base 510, including but not limited to the exemplary configurations shown in FIGS. 5B-5E. The dissolvable tubes 210 can be configured such that they pass through the base 510, as shown in FIG. 7.

An enclosure 710 may be affixed to or formed as part of the base 510 to form an enclosed volume that is provided in communication with the central lumens or openings at the proximal (non-pointed) ends of the tubes 210. The enclosed volume can also be provided in communication, e.g., with a pressure source 720, e.g., via a conduit 730 as shown in FIG. 7. For example, the pressure source 720 can include an electric pump, a deformable bulb, a reduced-pressure or vacuum line, or the like. The conduit 730 can be, e.g., a pipe, a tube, a flexible hose, or the like.

The exemplary apparatus 700 can provide a reduced pressure within the volume enclosed by the enclosure 710 and base 510 by activation of the pressure source 720. This can result in a lower pressure being present in the upper (proximal) portions of the tubes 210, which can facilitate removal of micrografts 120 (not shown in FIG. 7) from surrounding tissue via a suction action. It may be preferable to provide only a slight reduction of pressure within the closed volume, such that micrografts 120 can be harvested more easily and still remain within the tubes 210, but not pulled through the tubes 210 and into the enclosed volume (which could happen if the pressure within the enclosed volume were reduced significantly). An appropriate reduced pressure level can be determined easily without undue experimentation based on the length and diameter of the tubes 210, the type of tissue being harvested, the number of tubes 210 in the apparatus 700, etc.

Figure 8:
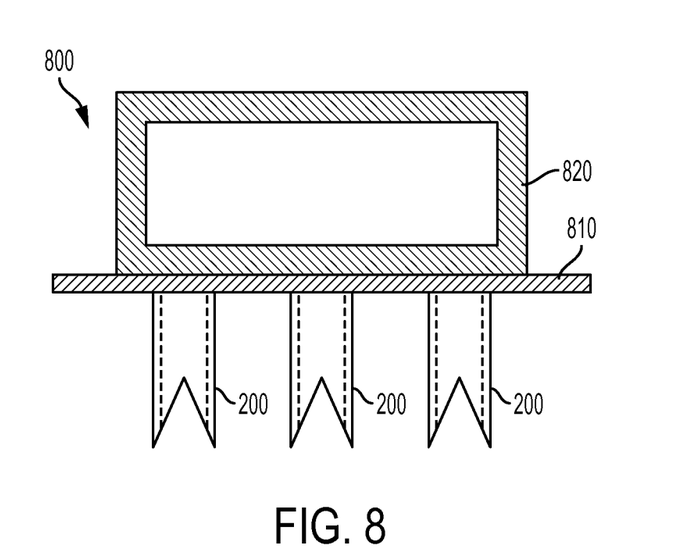
FIG. 8 is a schematic illustration of another exemplary apparatus that can be used to harvest and implant micrograft tissue in accordance with sill further exemplary embodiments of the present disclosure.

In a yet further exemplary embodiment of the present disclosure, an exemplary apparatus 800 for harvesting and implanting micrografts 800 can be provided as shown in FIG. 8. The apparatus 800 can include, e.g., a plurality of dissolvable tubes or hollow needles 210 that are affixed or mechanically coupled to a film 810. The film can be sufficiently thin and/or made of an appropriate material such that it is flexible or deformable. The upper side of the film 810 can be removably adhered to the lower side of a handle 820, e.g., using a weak adhesive or glue, a tacky substance, or the like. In further embodiments, the film 810 can be mechanically supported or reinforced by the handle 820, e.g., the handle 820 can be affixed to or adhered to peripheral portions or edges of the film 810 to stretch it or otherwise provide rigidity to the film 810, or the like. Again, the tubes 210 can be provided in various configurations, e.g., in a linear array, or in any one of various two-dimensional patterns along the base 510, including but not limited to the exemplary configurations shown in FIGS. 5B-5E.

In use, the apparatus 800 can be pressed onto a donor site 100 such that the tubes 210 penetrate into the tissue there to separate and remove micrografts 120 from the donor site, e.g., similar to the procedure shown in FIGS. 4A and 4B. The apparatus 800 can then be pressed onto a recipient site 400, e.g., similar to the procedure shown in FIG. 4C, to implant the tubes 210 containing micrografts 120 at the donor site 400. During these procedures, the handle 820 can provide mechanical support to the film 810 and tubes 210 to facilitate their manipulation during the harvesting and/or implantation procedures.

After the tubes 210 are inserted into the recipient site 400, the handle 820 can be removed from the film 810, to leave just the film 810 and dissolvable tubes 210 at the donor site 400. For example, the apparatus 800 can be configured such that a portion of the film 810 extends beyond the sides of the handle 820. After the tubes 210 have been implanted into the recipient site 400 (e.g., such that the film 810 contacts the surface of the recipient site 400), the protruding ends of the film 810 can be held down while the handle 820 is lifted away, such that only the film 810 and tubes 210 remain at the recipient site 400. The film 810 can act as a flexible patch that can be left in place over the implanted tubes 210 to cover the recipient site 400 after the micrografts 120 have been implanted.

In further embodiments, the film 810 and tubes 210 may be provided as a patch without the handle 820, e.g., where the film 810 may be flexible but strong enough to be handled directly. In another embodiment, the film 810 can be provided with one or more bioactive substances that may be released into the donor site 400 over time. Such substances can resist infection at the donor site 400, provide nutrients or other growth-affecting substances to enhance growth of the implanted micrografts 120, etc.

In certain embodiments, the base 510 or film 810 described in the various embodiments herein can also be made from a biodegradable or dissolvable material, such that it can be allowed to remain on the recipient site 400 and disappear over time. A dressing or covering can optionally be placed over the base 510 or film 810 after it has been applied to the recipient site. In further embodiments, the needles 210 and base 510 can be formed from different materials or compositions that may dissolve at different rates. For example, the needle material may dissolve relatively quickly, e.g., on the order of about a minute or several minutes or hours, whereas the base 510 may dissolve over a longer period and protect the underlying recipient site 400 for a period after the needles 210 have dissolved.

In a further embodiment, the needles 210 can be provided with notches 320 and/or thinned walls at or near where they are affixed to the base 510. After the apparatus has been inserted into the tissue at the recipient site 400, as shown in FIG. 6B, a lateral force or impact can be applied to the base 510 such that the needles 210 break off from the base 510. In this manner, the distal ends of the needles 210 containing micrografts 120 can be implanted in the recipient site 400, and the remainder of the apparatus 500 can be removed. Such notches 320 or thinned regions can be provided in the needles 210 or used in any of the embodiments described herein, e.g., to facilitate separation of the needles 210 from the base 510 or any other component that is configured to hold or position the needles 210 during the harvesting and/or implantation procedure. Again, the recipient site 400 can optionally be covered with a wound dressing or the like after the needles 210 have been implanted.

The exemplary methods and devices described herein can provide several benefits and advantages. For example, they can facilitate a simple procedure for harvesting, transporting, and implanting a plurality of micrografts or MTCs 120 as described herein, while also reducing or avoiding any direct handling of the micrografts 120. Such procedures and devices can better retain mechanical integrity and reduce the possibility of contamination of the micrografts 120. The exemplary methods and devices described herein can also implant the micrografts 120 in the recipient site 400 with the same orientation and relative locations as they had in the donor site 100 from which they were obtained. The implantation procedure can be more reliable and simpler, because the dissolvable needles 210 containing micrografts 120 are easier to place into a recipient site 400 than just the small, soft micrografts 120 by themselves. By providing needles 210 made of a dissolvable or biodegradable material, the needles 210 can be configured to precisely position the micrografts 120 within the donor site tissue and hold them in place, with the needles 210 subsequently dissolving.

A biodegradable and biocompatible material that can be used with exemplary embodiments of the disclosure is maltose, which has triple-state (liquid-glassy-solid) characteristics that can be altered by changing its temperature to facilitate shaping and manufacture of needle shapes. Other suitable materials that can be used in further exemplary embodiments include, but are not limited to, water soluble-soluble compositions such as polylactic-co-glycolic acid (PLGA), poly-vinyl pyrrolidone (PVP), and carboxymethyl cellulose (CMC). Such materials can be processed to form small needles 210 as described herein. Other biocompatible materials known in the art that have suitable mechanical properties and dissolution or decomposition properties can also be used with embodiments of the disclosure.

In further embodiments of the disclosure, materials used to form the needles 210 and/or base 510, if present, can include one or more bioactive or growth-enhancing additives that can be released at the donor site 400 as the needle material dissolves or decomposes. Such substances can include, but are not limited to, buffers, nutrients, cell growth factors, antibiotics, anti-inflammatory compositions, etc. Examples of growth factors include, but are not limited to, vascular endothelial growth factor (VEGF), platelet-derived growth factor (PDGF), transforming growth factor beta (TGF-β), and fibroblast growth factor (FGF), which may enhance or promote vascularization of the grafts. Epidermal growth factor (EGF) and keratinocyte growth factors can also be used, and may increase mobilization and differentiation of certain skin cells, such as keratinocytes and fibroblasts.

The needles 210 can be formed using known microfabrication techniques including, but not limited to, casting and solidification or polymerization of materials in a mold, MEMS manufacturing techniques, physical and/or chemical vapor deposition techniques, etc. The needles 210 can be formed as hollow tubes 210 with points 220 pre-formed, e.g., as part of a mold shape, or alternatively the points 220 can be formed by angled cutting or grinding of the end of hollow tubes 210 as described herein. In certain embodiments the needles 210 can be substantially cylindrical. In further embodiments, the needles 210 can be slightly tapered, e.g., with the distal, pointed end being somewhat narrower than the proximal end. In still further embodiments, a plurality of needles 210 and a base 510 can be formed as a single object, e.g., as a single cast or molded object.

In certain exemplary embodiments, the needles 210 and/or base 510, if present, can be porous. Porosity can enhance dissolution of the needle material. It can also facilitate transport of moisture, oxygen, and/or other substances to the micrograft 120 within a needle 210 prior to dissolution of the needle material, which can enhance viability and growth of the micrografts 120 after implantation. The extent of porosity may be limited by the intrinsic mechanical properties of the material used to form the needles 210, such that the needles 210 are sufficiently stiff to penetrate the biological tissue and resist fracture and/or undesirable shape distortions during insertion and withdrawal.

In further embodiments of the disclosure, the method and apparatus described herein can be used for tissue copying procedures. For example, the recipient site 400 can be an ex vivo scaffold or matrix material, instead of a region of a living subject's body. Such matrix materials can include, but are not limited to, polylactic acid (PLA), collagen (e.g., a collagen sponge), low melting agarose (LMA), hyaluronic acid (e.g., hyaluranon), or devitalized animal or cadaveric skin. In further embodiments, the matrix material for a recipient site 400 suitable for tissue copying can be formed of allogeneic skin that can be prepared, e.g., by freezing and thawing a portion of donor skin tissue several times. For example, about seven freezing/thawing cycles can be performed to effectively kill the cells in the source skin for use as a matrix. The frozen and thawed tissue can then be washed with a detergent or other composition to remove dead cells, debris, etc. Implantation of a plurality of MTCs or micrografts 120 in an ex vivo matrix that is maintained under suitable growth conditions can lead to integration and growth of the micrografts 120 in the matrix material, and may result in larger portions of "copied" tissue derived from the donor site 100.

In still further exemplary embodiments of the present disclosure, the exemplary methods and apparati described herein can be applied to other tissues besides skin tissue, e.g., internal organs such as a liver, a heart, other muscle tissue, and the like. Thus, micrografts 120 can be harvested from a variety of tissues while producing little damage to a donor site 100 and facilitating rapid healing thereof, and then placed or implanted at recipient sites 400, e.g. a damaged region of an organ or an ex vivo matrix material, in a direct manner.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure. All patents and publications cited herein are incorporated herein by reference in their entireties.

What is claimed is:

1. An apparatus for grafting at least one biological tissue, comprising:
   at least one hollow tube comprising at least two points or extensions provided at a distal end thereof,
   wherein an inner diameter of the at least one hollow tube is less than about 1 mm,
   wherein the at least one hollow tube comprises a biodegradable material,
   wherein at least one section of the at least one hollow tube is structured to be inserted into the at least one biological tissue at a donor site to remove at least one portion of a graft tissue therefrom when the at least one section of the at least one hollow tube is withdrawn from the donor site, and
   wherein the at least one hollow tube comprises a notch provided in a wall of the at least one hollow tube, wherein the notch is structured to facilitate breakage of the at least one hollow tube at a location of the notch, and wherein at least one section of the at least one hollow tube is structured to be inserted into a recipient site and subsequently broken off in the recipient site at the location of the notch to thereby place the at least one portion of the graft tissue within the recipient site.

2. The apparatus of claim 1, wherein an inner diameter of the at least one hollow tube is less than about 0.5 mm.

3. The apparatus of claim 1, wherein an inner diameter of the at least one hollow tube is less than about 0.3 mm.

4. The apparatus of claim 1, wherein the at least one hollow tube comprises at least three points or extensions provided at the distal end thereof.

5. The apparatus of claim 1, further comprising a plate provided within a lumen of the at least one hollow tube proximal to the distal end, the plate adjacent to the notch,
   wherein the plate obstructs at least a portion of the lumen, and
   wherein the plate is structured to retain the at least one portion of the graft tissue in a distal portion of the at least one hollow tube when the at least one hollow tube is inserted into the recipient site.

6. The apparatus of claim 5, wherein the plate comprises a biodegradable material.

7. The apparatus of claim 6, wherein the at least one hollow tube is structured to break at the location of the notch in response to a lateral force applied to the plate.

8. The apparatus of claim 1, further comprising a stop arrangement coupled to an outer portion of the at least one hollow tube to at least one of control and/or limit a distance to which the at least one hollow tube is inserted into the at least one biological tissue.

9. The apparatus of claim 1, further comprising a base arrangement, wherein the at least one hollow tube comprises at least two hollow tubes, and wherein the at least two hollow tubes are affixed to the base arrangement.

10. The apparatus of claim 9, wherein the base arrangement comprises a biodegradable material.

11. The apparatus of claim 9, further comprising a housing affixed to the base arrangement, wherein the housing is configured to facilitate manipulation of the base arrangement.

12. The apparatus of claim 11, wherein the housing is detachably affixed to the base arrangement.

13. The apparatus of claim 11, further comprising a low-pressure source, wherein the housing is configured to form an enclosed volume over at least a portion of the base arrangement;

wherein a lumen of each of the at least two hollow tubes is provided in communication with the enclosed volume; and wherein the low-pressure source is provided in communication with the enclosed volume.

14. The apparatus of claim 9, wherein the base arrangement is provided as a flexible film.

15. The apparatus of claim 14, further comprising a handle removably adhered to at least a portion of an upper surface of the film.

16. The apparatus of claim 1, wherein the biodegradable material comprises a porous material configured to dissolve at the recipient site.

17. The apparatus of claim 1, wherein the biodegradable material is configured to dissolve at the recipient site, via a chemical or physical mechanism.

18. The apparatus of claim 17, wherein the biodegradable material is configured to dissolve in response to activation via application of light energy, application of heat, or exposure to a biocompatible solvent.

19. The apparatus of claim 1, wherein the notch comprises a groove that extends partially or completely around the circumference of the at least one hollow tube.

20. The apparatus of claim 1, further comprising a plurality of notches disposed around the circumference of the at least one hollow tubes, the plurality of notches comprising indentations to the at least one hollow tube.

* * * * *